(12) United States Patent
Tsien et al.

(10) Patent No.: US 10,143,377 B2
(45) Date of Patent: Dec. 4, 2018

(54) SINGLE CHANNEL IMAGING MEASUREMENT OF DYNAMIC CHANGES IN HEART OR RESPIRATION RATE

(75) Inventors: Joseph Z. Tsien, Evans, GA (US); Meng Li, Augusta, GA (US); Fang Zhao, Hei-Long-Jiang Province (CN); Yi Qian, Yunnan Province (CN)

(73) Assignees: Augusta University Research Institute, Inc., Augusta, GA (US); Banna Biomedical Reseach Institute, Yunnan Province (CN)

( * ) Notice: Subject to any disclaimer, the term of this patent is extended or adjusted under 35 U.S.C. 154(b) by 0 days.

(21) Appl. No.: 13/462,524

(22) Filed: May 2, 2012

(65) Prior Publication Data

US 2013/0296660 A1 Nov. 7, 2013

(51) Int. Cl.
| | |
|---|---|
| *A61B 5/00* | (2006.01) |
| *A61B 5/0205* | (2006.01) |
| *A61B 5/024* | (2006.01) |
| *A61B 5/0255* | (2006.01) |
| *A61B 5/026* | (2006.01) |
| *G06T 7/00* | (2017.01) |

(52) U.S. Cl.
CPC ............ *A61B 5/004* (2013.01); *A61B 5/0077* (2013.01); *A61B 5/0205* (2013.01); *A61B 5/026* (2013.01); *A61B 5/0255* (2013.01); *A61B 5/02405* (2013.01); *G06T 7/0016* (2013.01); *A61B 5/4809* (2013.01); *G06T 2207/10048* (2013.01); *G06T 2207/30076* (2013.01)

(58) Field of Classification Search
None
See application file for complete search history.

(56) References Cited

U.S. PATENT DOCUMENTS

| | | | | |
|---|---|---|---|---|
| 5,206,140 | A | | 4/1993 | Marder |
| 5,218,962 | A | * | 6/1993 | Mannheimer et al. ....... 128/633 |
| 2004/0039268 | A1 | * | 2/2004 | Barbour et al. ............. 600/310 |
| 2008/0045847 | A1 | | 2/2008 | Farag |
| 2009/0141124 | A1 | | 6/2009 | Liu |
| 2010/0217139 | A1 | | 8/2010 | Pinter |
| 2011/0251493 | A1 | | 10/2011 | Poh |
| 2011/0311143 | A1 | | 12/2011 | Cennini |

FOREIGN PATENT DOCUMENTS

| | | |
|---|---|---|
| EP | 2438849 | 4/2012 |
| WO | 2007128916 | 11/2007 |

OTHER PUBLICATIONS

Francisco, "Thermal Imaging for Law Enforcement and Security, Post 9-11," Proceedings of SPIE, vol. 5071, pp. 453-464, 2003.*
Yeragani, "Diminished Chaos of Heart Rate Time Series in Patients with Major Depression," Biol Psychiatry, vol. 51, pp. 733-744, 2002.*
Bland and Altman, "Statistical Methods for Assessing Agreement between Two Methods of Clinical Measurement", Lancet 1:307-10 (1986).vbTab.
Comon, "Independent component analysis, a new concept", Signal Process. 36:287-314 (1994).
Hyvärinen and Oja, "A fast fixed-point algorithm for independent component analysis", Neural Comput. 9:483-92 (1997).
Mika, et al., "An advanced detrending method with application to HRV analysis," IEEE Trans. Biomed. Eng., 49:172-5(2002).
Takano and Ohta, "Heart rate measurement based on a time-lapse image," Med Eng Phys., 29:853-7(2007).
International Search Report for corresponding PCT application, PCT/US2013/029551, dated Jun. 11, 2013. GSV.
Hart, et al., "The detection of D-dimer in plasma by enzyme immunoassay: improved discrimination is obtained with a more specific signal antibody", Blood Coagul.Fibrinolysis, 5(2): 227-32 (1994).

* cited by examiner

*Primary Examiner* — G Steven Vanni
(74) *Attorney, Agent, or Firm* — Smith Gambrell & Russell LLP

(57) ABSTRACT

Methods for remotely measuring or monitoring one or more physiological parameters in a subject, such as blood volume pulse, heart rate, respiratory wave, or respiration rate, are provided. The methods include capturing a series of images of the subject, and processing the images to obtain physiological parameters of interest. These methods can be used to analyze single channel signals, including signals obtained from active night vision cameras. As a result, these methods can be used to measure or monitor one or more physiological parameters in both daylight and low-light conditions. Also provided are methods of removing false positives. Systems for remotely measuring or monitoring one or more physiological parameters in a subject, as well as methods of using thereof, are also provided.

8 Claims, 7 Drawing Sheets

SINGLE CHANNEL IMAGING MEASUREMENT OF DYNAMIC CHANGES IN HEART OR RESPIRATION RATE

FIELD OF THE INVENTION

The invention is generally related to methods and systems for the measurement and monitoring of one or more physiological parameters, including blood volume pulse, heart rate, respiratory wave, and respiration rate, in a subject.

BACKGROUND OF THE INVENTION

The accurate measurement and monitoring of physiological parameters, including blood volume pulse (BVP), heart rate (HR), respiratory wave (RW), and respiration rate (RR), plays an important role in a wide variety of applications in healthcare, psycho-physiological (polygraph) examinations, and sports training. In particular, dynamic changes in physiological parameters can reveal changes in the physiological status and function of a patient.

Traditional techniques for the measurement of physiological parameters require sensors to be attached to a subject. The attachment of sensors to a subject can cause undesirable skin irritation and discomfort. In particular, it may be undesirable to affix sensors to patients during sleep studies (when they may influence a subject's sleep patterns) or during sports training (when they may adversely influence an athlete's mobility). In some cases, contact-based measurements have also been shown to influence the underlying physiological parameter(s) being measured. As a result, there is a great interest in methods of measuring and monitoring physiological signals by non-contact means. While many methods of remotely measuring physiological parameters have been investigated, the ability to distinguish the physiological parameter(s) to be measured in a subject from background, such as environmental noises and movement artifacts, is deficient or limited.

Laser Doppler, microwave Doppler radar, and thermal imaging have been investigated for the remote measurement of physiological parameters with varying success; however, all of these systems require expensive and specialized hardware. The ability to measure physiological parameters, including HR and RR, using a conventional video camera has attracted recent interest. See, for example, Takano, C. and Ohta, Y. "Heart rate measurement based on a time-lapse image," *Medical Engineering & Physics,* 29:853-857(2007). Though attractive in principle, many of these methods accomplish noise reduction using linear filters, which are ineffective in the event that background noise falls within the same frequency band as the physiological signal of interest. Others have proposed using blind source separation for noise removal. See, for example, U.S. Patent Application Publication No. US 2011/0251493 to Poh, et al. However, blind source separation methods require a multi-channel signal input, restricting their applicability to processing signals collected using a camera which provides a multi-channel signal (such as a color camera that generates a Red, Green, and Blue multiple-channel signal). As a result, these methods cannot be used to determine physiological parameters in conditions when ambient light is insufficient to permit the use of a color camera, such as in a darkened room. Moreover, blind source separation does not provide a method of distinguishing false positives from actual results. Blind source separation will return false physiological parameters when an inanimate object, such as a drawing or picture of a human face, is imaged. This severely limits the applicability of blind source separation methods in many healthcare applications, as it cannot reliably indicate a loss of vital signs in a subject.

Therefore, it is an object of the invention to provide improved methods and systems for non-contact measuring one or more physiological parameters, including blood volume pulse, heart rate, respiratory wave, and respiration rate, in a subject, particularly in low-light conditions.

It is also an object of the invention to provide methods and systems for non-contact monitoring dynamic changes one or more physiological parameters, such as blood volume pulse, heart rate, respiratory wave, and respiration rate, in a subject, particularly in low-light conditions.

It is a further object of the invention to provide methods and systems for distinguishing false positives from actual results when non-contact measuring and monitoring one or more physiological parameters, such as blood volume pulse, heart rate, respiratory wave, and respiration rate, in a subject, particularly in low-light conditions.

SUMMARY OF THE INVENTION

Methods and systems for remotely measuring and monitoring one or more physiological parameters, such as blood volume pulse, heart rate, respiratory wave, and respiration rate, in a subject are provided.

Methods for remotely measuring and monitoring one or more physiological parameters in a subject include capturing a series of images of one or more subjects over a period of time. Images may be captured using any suitable camera or video camera, such as a color, monochrome, low-light, day/night infrared, thermal, thermal IR, carbon-metal-oxide-semiconductor (CMOS) camera, or charge-coupled device (CCD) camera. In certain embodiments, images are captured using a photodetector, such as a phototransistor or photodiode (or array of phototransistors and/or photodiodes), which produces a single channel optical signal. In preferred embodiments, the image acquisition device is a digital camera or video camera which produces a single channel image signal output, such as an active night vision camera.

The series of images are then analyzed. Image analysis includes localizing the position of the one or more subjects in the images, establishing a region of interest (ROI) in the images for each physiological parameter to be measured, and separating each ROI into two or more subsets. The image series is then processed to determine temporal pattern information that is inherently generated from a given rhythmic signal source in a subject, such as a heartbeat. A subset from each region of interest can be processed by spatially averaging the pixels in the subset of each image to yield a single observed time series over time. The single observed time series can then be processed to obtain values for the one or more physiological parameters of interest. Processing can include constructing an embedding matrix by a series of delay vectors from the observed time series, extracting underlying informative independent components from the embedding matrix, and processing one of these independent components (the signal source) to obtain an estimate for the physiological parameter of interest. Signal processing can also include other steps, such as detrending, normalizing, and combinations thereof, as required to improve data analysis.

In some embodiments, one or more additional subsets from each region of interest can be similarly processed. By comparing the values for physiological parameter of interest obtained from multiple subsets within a ROI, false positives can be removed.

Systems for measuring one or more physiological parameters are also described. The systems can include an image acquisition device, such as a night vision camera, an illumination source, such as a near IR light emitting diode, signal processing circuitry configured to analyze a series of signal channel images to obtain one or more physiological parameters, memory modules, data ports, transceivers, screens, and alerting means.

The methods and systems can be used in a variety of settings to measure or monitor one or more physiological parameters of interest. For example, the methods and systems can be utilized in a healthcare setting, such as a hospital, doctor's office, clinic, nursing home, or assisted living facility, to measure one or more physiological parameters of interest. The methods and systems can also be used to monitor dynamic changes in one or more physiological parameters over extended periods of time. For example, the methods and systems can be used to monitor a subject's blood volume pulse, heart rate, respiratory wave or respiration rate, or combinations thereof in a home, nursery, operating room, doctor's office, jail, hospital, nursing home, or assisted living facility over an extended period of time. In this way, subjects can be monitored for signs of, for example, cardiac arrest and respiratory distress.

The methods and systems can be used to measure one or more physiological parameters in a subject in a variety of lighting conditions. In particular, because the method can analyze a single channel image, such as that obtained from an active night vision camera, these methods and systems can be used to measure or monitor physiological parameters in low-light conditions. As a result, the methods and systems can be used to observe a subject throughout a day/night cycle in order to monitor one or more physiological parameters in a subject during sleep. In certain embodiments, the systems and methods are used to detect or prevent sudden infant death syndrome (SIDS), diagnose obstructive sleep apnea, or monitor the vitality of a sleeping subject.

BRIEF DESCRIPTION OF THE DRAWINGS

FIG. 3A illustrates a series of video frames of the upper body of a human subject recorded at night over a period of time ($t_0$-$t_n$). The rectangle superimposed on the subject's face indicates the region of interest for cardiovascular pulse measurement. The rectangle superimposed on the subject's chest indicates the region of interest for respiratory measurement. FIG. 3B illustrates the observed time series for cardiovascular pulse measurement (left) and respiratory measurement (right). FIG. 3C illustrates the separated source signals (independent components (ICs), IC1, IC2, and IC3) for cardiovascular pulse measurement (left) and respiratory measurement (right). FIG. 3D illustrates the recovered blood volume pulse (left) and respiratory wave (right).

FIG. 4A is a plot showing the difference in heart rate (heart rate measured using the reference method minus heart rate measured using the proposed method, $HR_{ref}$-$HR_p$, in beats per minute (bpm)) as a function of the average heart rate measured by the reference and proposed methods (in bpm). The subject was imaged in the daylight. The solid horizontal line indicates the mean for the data set; the dotted lines indicate the mean ±1.96 standard deviations. FIG. 4B is a plot showing the difference in respiration rate (respiration rate measured using the reference method minus respiration rate measured using the proposed method, $RR_{ref}$-$RR_p$, in breaths per minute) as a function of the average respiration rate measured by the reference and proposed methods (in breaths per minute). The subject was imaged in the daylight. The solid horizontal line indicates the mean for the data set; the dotted lines indicate the mean±1.96 standard deviations. FIG. 4C is a plot showing the difference in heart rate (heart rate measured using the reference method minus heart rate measured using the proposed method, $HR_{ref}$-$HR_p$, in beats per minute (bpm)) as a function of the average heart rate measured by the reference and proposed methods (in bpm). The subject was imaged in low-light conditions. The solid horizontal line indicates the mean for the data set; the dotted lines indicate the mean±1.96 standard deviations. FIG. 4D is a plot showing the difference in respiration rate (respiration rate measured using the reference method minus respiration rate measured using the proposed method, $RR_{ref}$-$RR_p$, in breaths per minute) as a function of the average respiration rate measured by the reference and proposed methods (in breaths per minute). The subject was imaged in low-light conditions. The solid horizontal line indicates the mean for the data set; the dotted lines indicate the mean±1.96 standard deviations.

FIG. 5A is a plot of the heart rate (in bpm) measured in a subject as a function of time (in seconds). FIG. 5B is a plot of the respiration rate (in breaths per minutes) measured in a subject as a function of time (in seconds). In both cases, physiological parameters were measured in a subject following moderate exercise. Values measured using the proposed method (dotted traces in FIGS. 5A-5B) and the reference method (solid traces in FIGS. 5A-5B) are overlayed in both figures, illustrating good agreement between values obtained using the proposed method and the reference method.

DETAILED DESCRIPTION OF THE INVENTION

I. Definitions

"Subject," as used herein, refers to an animal or portion thereof which can be visualized using the imaging equipment described herein. In certain embodiments, the subject is a human being. In other embodiments, the subject is a non-human animal, such as vertebrate, more preferably a mammal, such as a domesticated animal.

"Physiological parameter," as used herein, refers to a characteristic index of physiological signal that can be measured and monitored from a living subject. Examples of physiological parameters include blood volume pulse, heart rate, respiratory wave, and respiration rate.

"Blood volume pulse" (BVP), as used herein, refers to phasic change in blood volume in a given body region (e.g., a wrist or foot) that results from beating of the heart. Blood volume pulse is also referred to as cardiovascular pulse.

"Heart rate" (HR), as used herein, refers to the number of times over a fixed period of time that the heart completes a cardiac cycle. In certain cases, heart rate refers to the number of times in minute that the heart completes a cardiac cycle.

"Respiratory wave" (RW), as used herein, refers to the waveform of the body motion of a subject due to respiration.

"Respiratory rate" (RR), as used herein, refers to the number of breaths taken by a subject over a fixed period of time. In certain cases, respiratory rate refers to the number of breaths taken by a subject over a period of one minute. Respiratory rate is sometimes clinically referred to as respiration rate, pulmonary ventilation rate, ventilation rate, or breathing frequency.

"Region of interest" or ROI, as used herein, refers to a region within an image or series of images which is analyzed for the purposes of determining a given physiological parameter.

"Low-light," as used herein, refers to an ambient illuminance limit of less than or equal to 3.4 lux, more preferably less than or equal to 1.0 lux, most preferably less than or equal to 0.1 lux.

"Non-contact," as used herein, refers to methods of measuring and/or monitoring a physiological parameter in a subject that are performed without physically contacting the subject with a sensor.

II. Methods of Measuring and Monitoring Physiological Parameters

Figure 1:
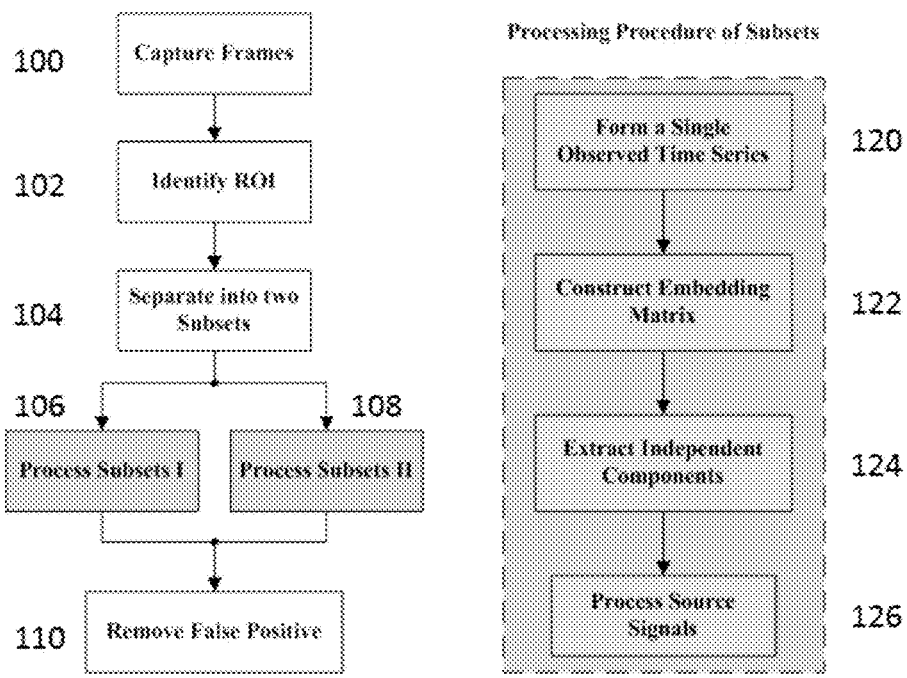
FIG. 1 is a schematic diagram illustrating methods for non-contact measuring and monitoring one or more physiological parameters in a subject.

A general method for non-contact measuring and monitoring one or more physiological parameters of interest is schematically represented in FIG. 1. First, images of a subject are collected over a period of time (step 100). The images are then analyzed to identify regions of interest (ROIs) for each physiological parameter to be measured within the images (step 102). Each ROI is subsequently divided into two or more subsets (step 104). The first subset obtained from each ROI can then be processed to obtain the corresponding physiological parameter (step 106). Signal processing includes forming a single observed time series over time from a series of captured images (step 120), constructing an embedding matrix by a series of delay vectors from the observed time series (step 122), extracting underlying informative independent components from the embedding matrix (step 124), and processing the source signal selected from independent components to obtain a value for the physiological parameter of interest (step 126). False positives can subsequently be removed by evaluating the difference between values obtained by analysis of the two or more subsets (step 110).

A. Image Capture

Methods for non-contact measuring and monitoring one or more physiological parameters involve capturing a series of images over time using an image acquisition device, such as a still camera or video camera.

Any suitable camera may be used to capture a series of images of the subject of interest over time. An appropriate camera for image capture can be selected in view of a number of factors, including the subject being measured or monitored, the ambient illuminance under which images are being collected, the time span over which images are being collected, the desired interval between images in the image series, and the intended setting in which measurement and monitoring is occurring.

Generally, the image acquisition device is a digital camera or video camera. The image capture device may be a color, monochrome, low-light, day/night infrared, thermal, thermal IR, carbon-metal-oxide-semiconductor (CMOS) camera, or charge-coupled device (CCD) camera. In preferred embodiments, the image acquisition device is a digital camera or video camera which produces a single channel image signal output. In embodiments where the image acquisition produces a multichannel image signal output, the image signal may be converted to a single channel image prior to analysis and signal processing. Alternatively, when the image acquisition device produces a multichannel image signal output, a single channel of the multichannel image may be analyzed and processed as described below to obtain the desired physiological parameters.

In preferred embodiments, the image acquisition device is a camera that is sensitive to light in the visible and near infrared region (i.e., between about 400-1,000 nm). For example, the image acquisition device may be an active infrared night vision camera. Active infrared night vision cameras combine infrared illumination within the spectral range of between about 700-1,000 nm (just below the visible spectrum of the human eye) with a charge-coupled device (CCD) camera or other camera sensitive to light in this spectral region as well as the visible spectral region. Exemplary night vision cameras include those available from Aptina Imaging Corporation (San Jose, Calif.), such as a model MT9V024 image sensor. Generally, the night vision cameras are used in conjunction with a light source during image capture. Suitable light sources for use in conjunction with these night vision cameras include near infrared light emitting diodes (LEDs).

Images may be collected over any suitable period of time, with the proviso that the images should be collected over a time period greater than at least one physiological signal length. In some cases, images are collected over a short period of time to measure one or more physiological parameters in a subject. In certain embodiments, the images are collected over a period of time between about three seconds and about five minutes in length, more preferably between about ten seconds and about two minutes in length, most preferably between about ten seconds and about one minute in length.

In some embodiments, images are collected over an extended period of time to monitor dynamic changes in one or more physiological parameters over time. In certain cases, images may be collected over a period of time between about five minutes and about twelve hours in length, more preferably between about one hour and about twelve hours in length, most preferably between about five hours and about twelve hours in length. In some cases, images are collected over a period of time greater than twelve hours, such as over one or more days.

The images may be collected in a variety of lighting conditions, depending upon the image acquisition device utilized and the subject(s) being monitored. For example, the images may be collected in daylight or low-light. In certain embodiments, the images are collected under an ambient illuminance limit of less than or equal to about 1,000 lux, less than or equal to about 500 lux, less than or equal to about 100 lux, or less than or equal to about 80 lux. In particular embodiments, the images are collected in low-light under an ambient illuminance limit of less than or equal to about 3.4 lux, more preferably less than or equal to 1.0 lux, most preferably less than or equal to 0.1 lux. Images may be collected over a period of time in which lighting conditions vary, such as over a 24 hour period. In particular embodiments, images are collected throughout the course of a subject's sleep cycle (Le., over a period of time beginning when the subject goes to bed and ending when the subject awakens).

The images are collected at regular time intervals over a suitable period of time. According to Nyquist sampling theorem, the sampling frequency should be at least twice the highest frequency contained in the signal. For example, a sampling rate of 8 Hz can be used to measure or monitor a heart rate up to 240 bpm. The maximum sampling frequency will generally be equal to the highest frame rate of the image acquisition device (e.g., a camera).

In some instances, a single subject is imaged. Alternatively more than one subject may be imaged. In instances where more than one subject is imaged, the image series may be processed to determine one or more physiological parameters in a single subject with the images, or to determine one or more physiological parameters in multiple subjects within the images.

B. Signal Processing

A series of images of a subject captured over time are subsequently processed to determine one or more underlying physiological parameters of interest. All of the images captured may be processed; alternatively, a subset of the images captured may be processed. However, the series of images processed must span a period of time greater than one physiological signal length.

Signal processing typically begins by identification of one or more subjects within the image series. In some cases, the series of images contains a single subject of interest; however, in other instances; the series of images may contain more than one subject to be measured or monitored. Subjects may be manually identified within the images; however, in preferred embodiments, the one or more subjects are automatically identified within the images, for example, using a boosted cascade classifier to detect the position of the subjects.

Cascade architectures contain a set of classifiers which are arranged in a cascade in order of increasing complexity. Each successive classifier is applied only on those selected portions of the images which pass through the preceding classifiers, and are considered likely to contain a subject or region of interest. Other suitable methods for the detection of one or more subjects in a series of images are known in the art, and include skin detection, Edge-Orientation Matching (EOM), Support Vector Machine (SVM), Neural Network-Based Approach, Information-Based Maximum Discrimination, Multi-Threaded Approach, and Subspace Discriminant Wavelet Features.

Once the one or more subjects of interest are identified, a region of interest for each physiological parameter to be measured is then selected within the images in the image series. The region of interest may be manually defined within the images; however, in certain embodiments, the region of interest in automatically determined for each physiological parameter. For example, a region of interest for a desired physiological parameter may be automatically defined using a boosted cascade classifier to detect the body part of a subject or skin detection to find skin-colored regions in a subject.

The region of interest may have any suitable shape, as dictated by the subject being observed, physiological parameter being monitored or measured, and the nature of the images obtained. For example, the region of interest may be circular, ovular, or polygonal (e.g., triangular, quadrilateral, such as a square or rectangular, pentagonal, hexagonal, etc.). In certain embodiments, the region of interest is a rectangular region within the series of images.

In certain embodiments, the physiological parameter being measured or monitored is the subject's blood volume pulse and/or heart rate, and the region of interest is the area of the subject's skin, such as the subject's face, arm, wrist, or a portion or combination thereof. In some embodiments, the physiological parameter being measured or monitored is the subject's respiratory wave and/or respiratory rate, and the region of interest is the area of the subject's body which moves as a consequence of respiration, such as the subject's chest, abdomen, or a portion or combination thereof.

Once defined, each region of interest is subsequently divided into two or more subsets. In certain embodiments, each ROI is divided into two subsets. The two or more subsets are defined within the region of interest such that each subset has an area smaller than the total of the region of interest, and the two subsets are defined within the region of interest such that they are not identical, but substantially overlap. For example, in some cases, the region of interest is a rectangular region within a series of images. In certain cases, a rectangular region of interest is divided into two subsets: a first subset drawn from the upper left corner of the ROI with a height equal to 90% of the height of the ROI and a width equal to 90% of the width of the ROI, and a second subset drawn from the lower left corner of the ROI with a height equal to 90% of the height of the ROI and a width equal to 90% of the width of the ROI.

Generally, the area of each subset is at least 70% of the area of the region of interest, more preferably at least 75% of the area of the region of interest, most preferably at least 80% of the area of the region of interest.

In certain embodiments, the two subsets substantially overlap in area, such that the two subsets with a region of interest share at least 50% of their area in common, more preferably at least 65% of their area in common, most preferably at least 75% of their area in common.

Next, a measurement point for each physiological parameter is obtained from each image within the series of images by spatially averaging the brightness of the pixels in the subset. Spatial averaging can be accomplished by computing a spatial mean, median, or mode. The average brightness obtained for each subset in a series of images over time are then combined to yield a single observed time series.

If desired, detrending and normalization can then be applied to the observed time series. For example, the observed time series can be detrended using suitable methods, such as a smoothness priors approach. Alternative statistical methods known in the art, such as polynomial fitted methods and filtering methods such as median filter, FIR filter, and wavelet transfonn may also be used in the detrending step.

When detrending using the smoothness priors approach, suitable detrending parameters can be selected in view of the frequency characteristic and sampling rate of the physiological parameter being measured or monitored. See, for example, Mika, P. Perdu, O. Ranta-aho and Pasi, A. Karjalainen. "An advanced detrending method with application to HRV analysis," *IEEE Trans. Biomed. Eng.,* 49:172-175 (2002). For example, when the sampling rate is 15 Hz and the physiological parameter being measured is a human subject's heart rate, the detrending parameter can be $\lambda=20$, corresponding to a cutoff frequency of 0.62 Hz. Similarly, when the sampling rate is 15 Hz and the physiological parameter being measured is a human subject's respiratory rate, the detrending parameter can be $\lambda=300$, corresponding to a cutoff frequency of 0.17 Hz.

The observed time series also optionally be normalized using statistical methods known in the art. In certain embodiments, the observed time series is normalized to zero-mean and unit variance as $$x'(t) = [x(t) - \mu]/\sigma$$

where $\mu$ and $\sigma$ are the mean and standard deviation of x(t), respectively.

Next, the observed time series is processed using dynamical embedding (DE). In this step, an embedding matrix is constructed from a series of delay vectors taken from the observed time series $x_i = x(i\tau_s)$, where $\tau_s$ is the sampling time of the observed signal x(t). The resulting DE matrix is shown below $$X = \begin{bmatrix} x_1 & x_{1+d} & \cdots & x_{1+nd} \\ x_{1+d} & x_{1+2d} & \cdots & x_{1+(n+1)d} \\ \vdots & \vdots & & \vdots \\ x_{1+(m-1)d} & x_{1+md} & \cdots & x_{1+(m+n-1)d} \end{bmatrix}$$

where m is the embedding dimension, $\tau_d = d\tau_s$ is the time delay. In preferred embodiments, the delay vector size should be no greater than or equal to two. The number of delay vectors n is determined by the length of the observed signal to be analyzed; however, the number of delay vectors must be at least as large as one physiological signal. In certain embodiments, the time delay is equal to the total timespan of the observed time series.

The DE matrix is then processed to deconstruct the observed time series into its underlying independent components. The DE matrix can be deconstructed using, for example, independent component analysis (ICA). ICA is a statistical technique for uncovering independent sources from a set of observation. See, for example, Comon, P. *Signal Process.* 36:287-314 (1994). By performing independent component analysis on the DE matrix, the single raw signal can be deconstructed into a group of independent source signals. In this way, the underlying physiological signals are separated from the various sources of noise.

Any suitable ICA algorithm may be utilized. In certain embodiments, fast ICA is utilized to extract the underlying source signals in the embedding matrix. Hyvärinen, A. and Oja, E. *Neural Comput.* 9:483-492 (1997). Fast ICA is well suited to this method because of both its ease and high speed of implementation. The fast ICA model assumes that the observed signal is a linear mixture of the underlying source signals, that is, Y=AX where X is an m×n matrix containing the independent source signals, and A is the m×m mixing matrix. Fast ICA is to find a separating or de-mixing matrix W, such that $\hat{X}$=WY is an estimate of X. W must maximize the non-Gaussianity of each source to uncover the independent source signals. Other suitable ICA algorithms suitable for use are known in the art, and include Joint Approximate Diagonalization of Eigen values (JADE), Infomax, and RunICA.

The independent component whose power spectrum contained the highest ratio of peak to total energy was then selected as the source signal for further analysis. In preferred embodiment, moving average filtering is performed on source signal to obtain waves for the physiological parameter of interest. Subsequently, multi-layer autocorrelation and fast Fourier transformation can be utilized to obtain the frequency of physiological parameter of interest.

If desired, one or more additional subsets from each region of interest can be similarly processed. By comparing the values for physiological parameter of interest obtained from multiple subsets within a ROI, false positives can be removed. For example, in cases when the physiological parameter being measured is a human subject's heart rate, the difference between the values obtained from two subsets can be compared to a threshold value. In cases when the difference is less than or equal to the threshold, the value is judged as a true positive. In cases where the difference is greater than the threshold, the value is judges as a false positive, and removed. In certain embodiments, the threshold is less than or equal to about 5 bpm, more preferably less than or equal to about 3 bpm, most preferably less than or equal to about 2 bpm.

C. Physiological Parameters

In principle, any physiological rhythmic pattern buried among various other signals or environmental noise, should possess a characteristic pattern which can be uncovered from the raw signal, as described above. The methods can be employed to measure or monitor a single physiological parameter in a subject, or simultaneously measure more than one physiological parameter in a subject.

Exemplary physiological parameters that can be measured or monitored include blood volume pulse, heart rate, respiratory wave, respiration rate, and combinations thereof.

The methods can also be used to measure one or more physiological parameters in a portion of a subject, such as an organ, tissue, or cell. For example, the methods can be used to measure or monitor the contraction rate of a cardiac cell in culture or a harvested heart organ.

III. Systems

Systems for the remote determination of one or more physiological parameters in a subject include an image acquisition device. An appropriate image acquisition device can be chosen in view of a number of factors, including the subject being measured or monitored, the ambient illuminance under which images are being collected, the time span over which images are being collected, the desired interval between images in the image series, and the intended setting in which measurement and monitoring is occurring. Generally, the image acquisition device is a digital camera or video camera. The image capture device may be, for example, a color, monochrome, low-light, day/night infrared, thermal, thermal IR, carbon-metal-oxide-semiconductor (CMOS) camera, or charge-coupled device (CCD) camera. In preferred embodiments, the image acquisition device is a digital camera or video camera which produces a single channel image signal output. In another embodiment, the image acquisition device is a photodetector, such as a phototransistor, a photodiode, or combinations thereof, that serve to collect an optical signal.

In preferred embodiments, the image acquisition device is a camera that is sensitive to light in the visible and near infrared region (i.e., between about 400-1,000 nm). For example, the image acquisition device may be an active infrared night vision camera. Active infrared night vision cameras combine infrared illumination within the spectral range of between about 700-1,000 nm (just below the visible spectrum of the human eye) with a charge-coupled device (CCD) camera or other camera sensitive to light in this spectral region and the visible spectral region. Exemplary night vision cameras include those available from Aptina Imaging Corporation (San Jose, Calif.), such as a model MT9V024 image sensor. Generally, the night vision cameras are used in conjunction with a light source during image capture. Suitable light sources for use in conjunction with these night vision cameras include near infrared light emitting diodes (LEDs).

The system can further include signal processing circuitry, a processor, or combinations thereof configured to process the digital images to obtain one or more physiological parameters, as described above. The system can also include integrated a memory module, such as a ROM or flash memory module, that can store executable software (e.g., for signal processing and data analysis) and data.

The system can include one or more data ports suitable to interface the system to an external device, such as a personal computer, cellular phone, or tablet personal computer, or display screen. The system may also include one or more wireless transceivers, such as a Bluetooth® or WiFi® transceiver, to interface the system to an external device, such as a personal computer, cellular phone, tablet personal computer, or display screen.

Data ports and wireless transceivers may be used to transmit processed data obtained from subject, such as one or more physiological parameters. Data ports and wireless transceivers may also be used to download raw data obtained from a subject that can be remotely processed, for example using a personal computer, to obtain one or more physiological parameters. Data ports and wireless transceivers may also be used to control data acquisition, or to observe real-time images of a subject.

In some cases, the system further includes a display screen which displays one or more physiological parameters being measured. The display screen may display numerical values for one or more physiological parameters, a graph illustrating the values for one or more physiological parameters over time, maximum and minimum values measured for one or more physiological parameters, and combinations thereof.

The system may further include one or more means of signaling a physician, caretaker, or attendant when one or more physiological parameters changes or reaches a predetermined level. Examples of suitable signaling means include lights, audible alarms, or combinations thereof. The system may also be configured to alert an individual remotely when one or more physiological parameters changes or reaches a predetermined level. For example, the system may be designed to page, call, email, text message, or otherwise contact a physician, caretaker, or attendant when one or more physiological parameters changes or reaches a predetermined level.

IV. Methods of Use

The methods and systems described herein can be used in a variety of settings to measure or monitor one or more physiological parameters of interest. For example, the methods and systems can be utilized in a home, jail, dorm, military camp, sports facility, exercise room, or healthcare setting, such as a hospital, doctor's office, clinic, nursing home, or assisted living facility, to measure one or more physiological parameters.

The methods and systems can also be used to monitor dynamic changes in one or more physiological parameters over extended periods of time. For example, the methods and systems can be used to monitor a subject's blood volume pulse, heart rate, respiratory wave, respiration rate, or combinations thereof in a home, nursery, operating room, doctor's office, jail, hospital, camp, dorm, sport facility, nursing home, or assisted living facility over an extended period of time. In this way, subjects can be monitored for signs of, for example, cardiac arrest and respiratory distress.

The methods and systems can be used to measure one or more physiological parameters in a subject in a variety of lighting conditions. In particular, because the method can analyze a single channel image, such as that obtained from an active night vision camera, these methods and systems can be used to measure or monitor physiological parameters in low-light conditions. As a result, the methods and systems can be used to observe a subject throughout a day/night cycle in order to monitor one or more physiological parameters in a subject during sleep. In certain embodiments, the systems and methods are used to detect or prevent sudden infant death syndrome (SIDS), diagnose obstructive sleep apnea, or monitor the vitality of a sleeping subject.

These methods and systems can be designed to monitor a single subject over a period of time. Alternatively, the methods and systems can be used to monitor multiple subjects over a period of time. For example, a single system can be positioned within a room, such as a hospital room or hospital nursery, to simultaneously monitor one or more physiological parameters in multiple subjects simultaneously.

EXAMPLES

Example 1

Simultaneous Measurement of Heart Rate and Respiration Rate in both Daylight and Low-Light Conditions Fifteen subjects (7 males, 8 females) with different skin color (Caucasians, African Americans, and Asians) between ages of 27-50 years were participated in the experiments at Georgia Health Sciences University. Indoor ambient light and a near infrared LED (830 nm) served as source of illumination for daytime and nighttime tests, respectively. Subjects were seated in front of a night vision camera (model MT9V024 available from Aptina Imaging Corporation) at a distance of approximately 1 m to restrict their upper body within the visual angle of camera.

Figure 2:
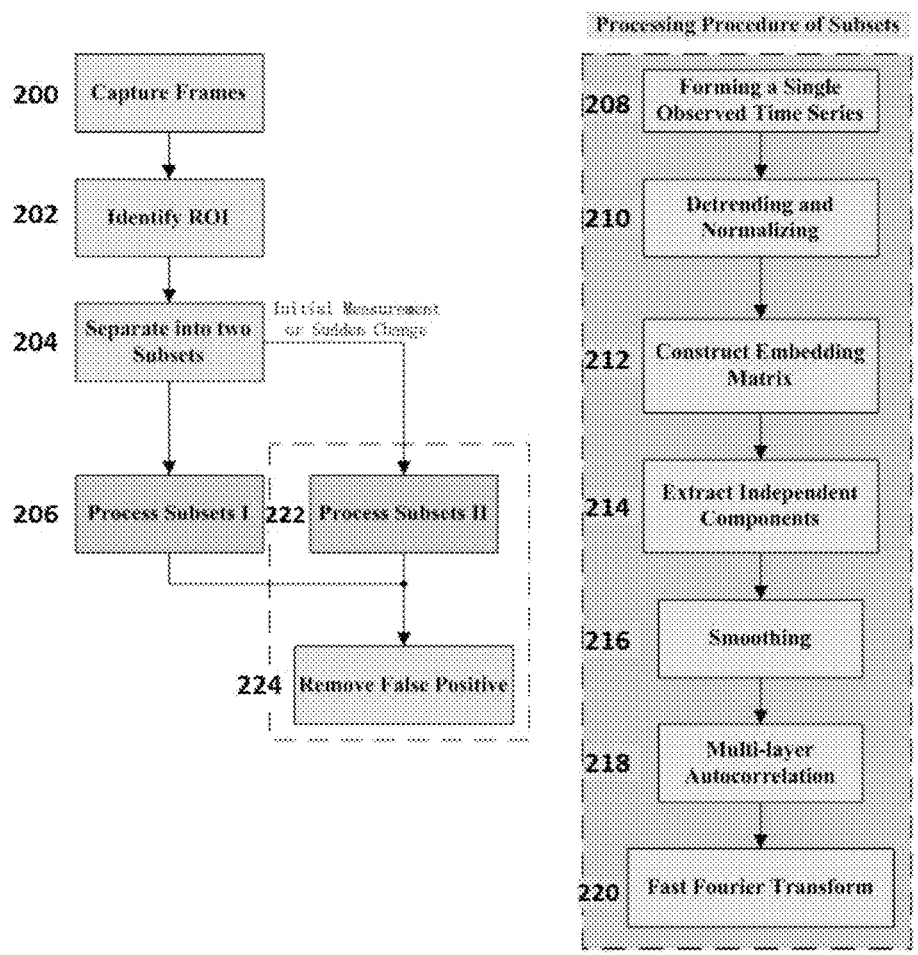
FIG. 2 is a schematic diagram illustrating the method used in Examples 1-3 to non-contact measure and monitor physiological parameters in a human subject.

The general strategy employed for data collection and analysis is generally described in FIG. 2. First, subjects were continuous filmed to obtain a series of images over time (step 200). Next, the images were analyzed to identify two regions of interest (ROIs) within the image series: one ROI used to determine blood volume pulse and heart rate, and a second ROI used to determine respiratory wave and respiration rate (step 202). Each ROI was subsequently divided into two subsets (step 204). The first subset obtained from each ROI was then processed to obtain the corresponding physiological parameter (blood volume pulse and heart rate or respiratory wave and respiration rate, step 206). The signal processing of step 206 included forming a single observed time series over time from a series of captured images (step 208), detrending and normalizing the observed time series (step 210), constructing an embedding matrix by a series of delay vectors from the detrended and normalized observed time series (step 212), performing independent component analysis on the embedding matrix (step 214), smoothing the selected source signal using moving average filter (step 216), implementing multi-layer autocorrelation (step 218), and obtaining the desired physiological parameter through fast Fourier transformation (step 220). In the case of initial measurements or a sudden change between adjacent measurements, the second subset for each ROI was processed using the same methodology employed for the first subset (step 222). False positives were removed by comparing the difference between the estimates for a physiological parameter obtained by independent analysis of each subset (step 224).

Subjects were continuously filmed for a period of three minutes. During image capture, subjects were instructed to face the camera, remaining seated, and breathe spontaneously. Subjects were allowed to move naturally within a small range, such as looking up/down, nodding, tilting the head or making some facial expressions. During the period of image capture, electrocardiography (ECG) and respiratory signals were collected using an OmniPlex® data acquisition system (Plexon, Inc.) at a sampling rate of 1 kHz.

Figure 3A:
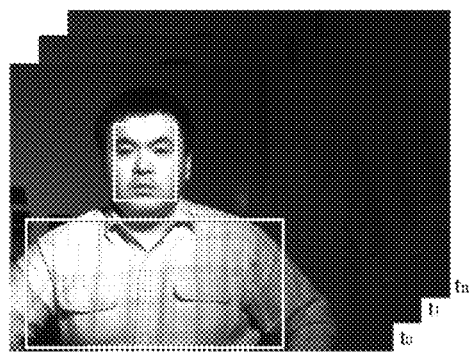
FIGS. 3A-3D illustrate methods of image capture and signal processing used to remotely obtain one or more physiological parameters from a subject.

Real-time data acquisition and processing were realized by software written in Visual C++. Image sequences of each subject were captured at 15 frames per second (fps) with pixel resolution of 640×480. The Open Computer Vision (OpenCV) library was utilized to automatically detect the face and upper body location in the first frame of each image sequence using a boosted cascade classifier. Based on the returned coordinates, we selected 90% height and 60% width of face area as the ROI for cardiovascular pulse measurement, and the area between the bottom of face and upper body as the ROI for respiration. The ROIs are outlined by rectangles in FIG. 3A. Each ROT was separated into two overlapping subsets, with the upper left 90% width and height of the ROI as the first subset and the lower right 90% width and height of the ROI as the second subset.

Figure 3B:
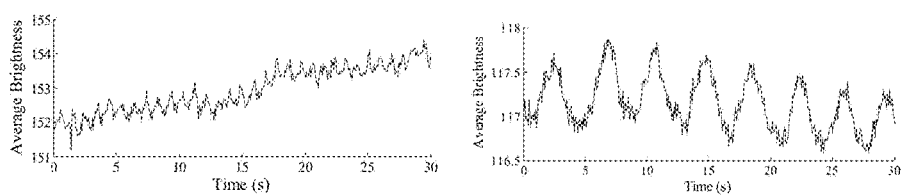

The average brightness in the subset was calculated for each frame to form single observed time series over time from recorded frames, as shown in FIG. 3B. The processing time window was half minute long. The observed time series was then detrended using a smoothness priors approach. The detrending parameters λ=20 and λ=300 were selected for analysis of the cardiovascular pulse ROI and respiration rate ROI, respectively. Each observed time series was then normalized to zero-mean and unit variance as $$x'(t)=[x(t)-\mu]/\sigma$$

where μ and σ are the mean and standard deviation of x(t), respectively.

Figure 3C:
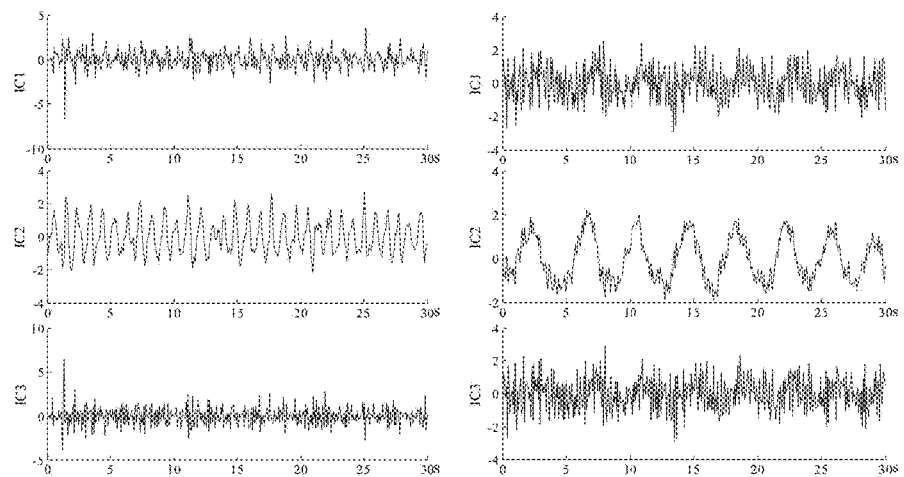

Using the delay reconstruction, the normalized observed time series were then constructing an embedding matrix with a delay of d=1 and m=3. Fast independent component analysis (ICA) was then performed to decompose embedding matrix into three independent source signals, as shown in FIG. 3C. The separated component whose power spectrum contained the highest ratio of peak to total energy was then selected for further analysis.

Figure 3D:
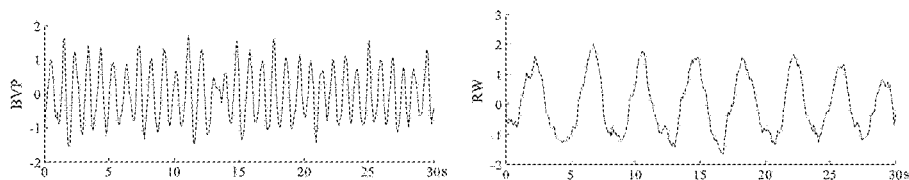
Figure 3E:
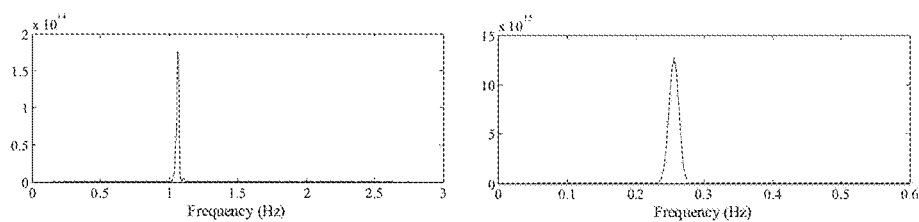
FIG. 3E is a plot showing the frequency (Hz) of the blood volume pulse (left) and respiratory wave (right).

The selected source signal was smoothed using a moving average filter (five-point for cardiovascular pulse and thirteen-point for respiration) to obtain cardiovascular pulse wave and respiratory wave, as shown in FIG. 3D. Three-layer autocorrelation was then performed to reduce the residual noise. Finally, a fast Fourier transform (FFT) was performed on the selected source signal to obtain the frequency spectrum. The frequency of physiological parameters was designated as the frequency that corresponded to the highest power of the spectrum, as shown in FIG. 3E.

In the first 30 seconds, both subsets for each ROI were measured to remove any potential false positives. One subset for each ROI was processed for further measurement and/or monitoring until a sudden change was observed. When a sudden change was observed, the second subset for the ROI was analyzed and compared to remove potential false positives.

Figure 4A:
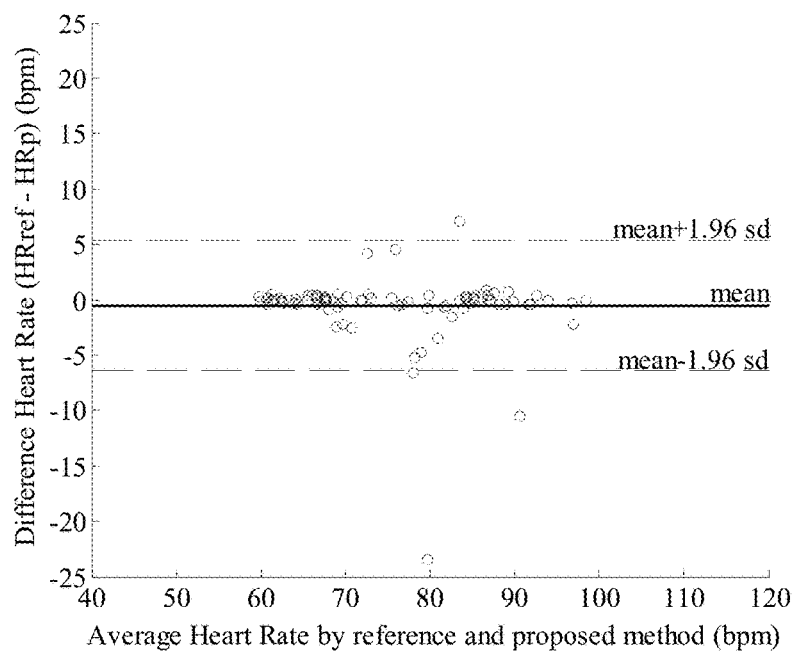
FIGS. 4A-4D are Bland-Altman plots comparing the values obtained for physiological parameters of interest using the image analysis methods described in Example 1 ("the proposed method") to values obtained using a contact reference method (an OmniPlex data acquisition system, "the reference method") under different lighting conditions.
Figure 4B:
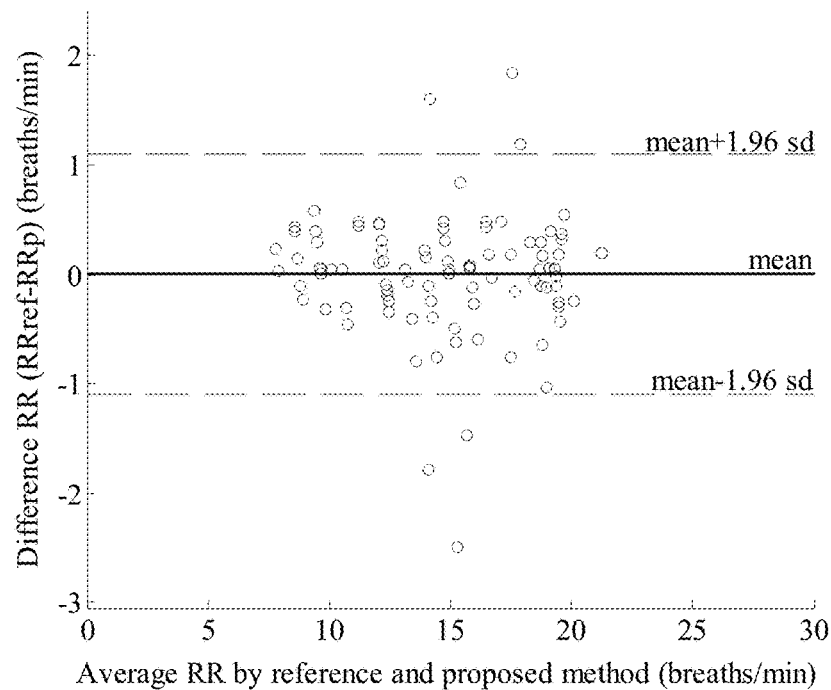
Figure 4C:
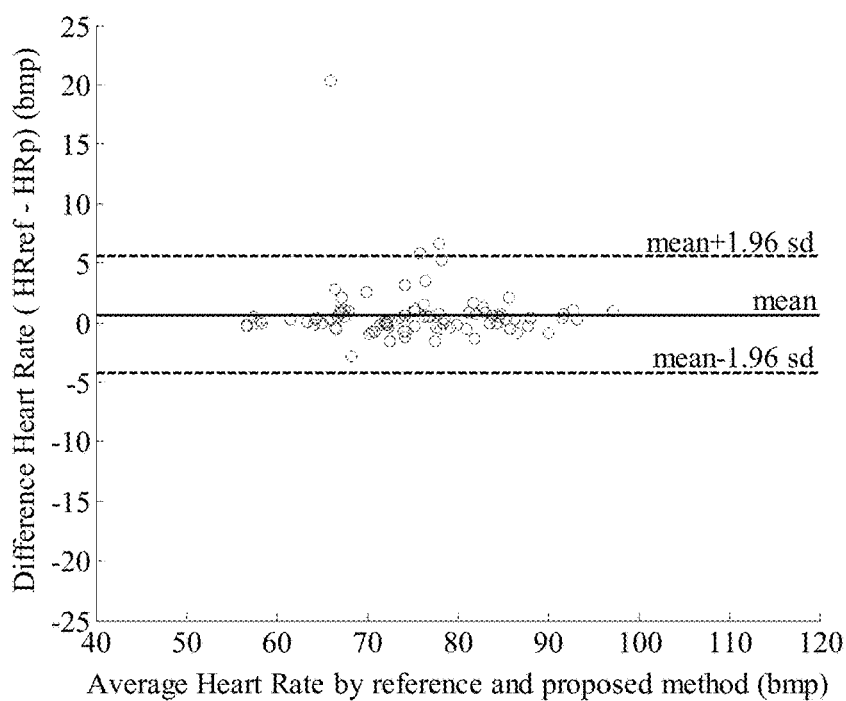
Figure 4D:
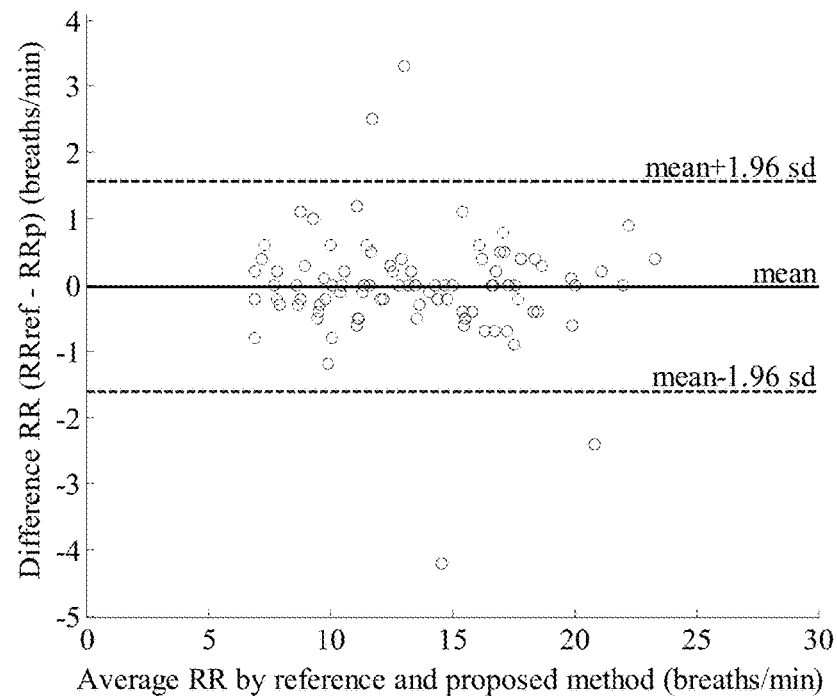

The degree of agreement between 95 pairs of measurements for heart rate and respiration rate from 15 subjects, measured by the method described above and by a conventional OmniPlex® data acquisition system (Plexon, Inc.), was determined by Bland-Altman analysis. See, for example, Bland, J. M. and Altman, D. G. "Statistical Methods for Assessing Agreement between Two Methods of Clinical Measurement" *Lancet* 1:307-10 (1986). The differences between measurements made via image analysis and measurements made using a conventional reference system were plotted against the averages of both systems (FIGS. 4A-4D). For night measurement, the mean bias $\bar{d}$ for heart rate was −0.54 with 95% confidence interval −6.56 to 5.48 bpm (FIG. 4A), the root mean square error (RMSE) was 3.13 bpm and the correlation coefficient r was 0.96 (p<0.001). For low-light measurement of the respiratory rate, the mean bias was 0.01 with 95% confidence interval −1.12 to 1.13 breaths/min (FIG. 4B), the root mean square error (RMSE) was 0.06 breaths/min and the correlation coefficient r was 0.99 (p<0.001). For daytime measurements, the mean bias for heart rate was 0.68 with 95% confidence interval as shown in FIG. 4C. The root mean square error (RMSE) was 3.10 bpm and the correlation coefficient r was 0.95 (p<0.001). For daytime measurements of the respiratory rate, the mean bias $\bar{d}$ was −0.02 with 95% confidence interval as shown in FIG. 4D. The root mean square error (RMSE) was 0.09 breaths/min and the correlation coefficient r was 0.98 (p<0.001).

Example 2

Dynamic Measurement of Heart Rate and Eespiration Rate in a Subject

A participant first performed moderate exercise (50 push-ups), and then was seated in front of a night vision camera (model MT9V024 available from Aptina Imaging Corporation) at a distance of approximately 1 m to restrict their upper body within the visual angle of camera. The subject was continuously filmed for a period of five minutes. During image capture, the subject were instructed to face the camera, remaining seated, and breathe spontaneously. The subject was allowed to move naturally within a small range, such as looking up/down, nodding, tilting the head or making some facial expressions. During the period of image capture, electrocardiography (ECG) and respiratory signals were also collected using an OmniPlex® data acquisition system (Flexon, Inc.) at a sampling rate of 1 kHz.

Figure 5A:
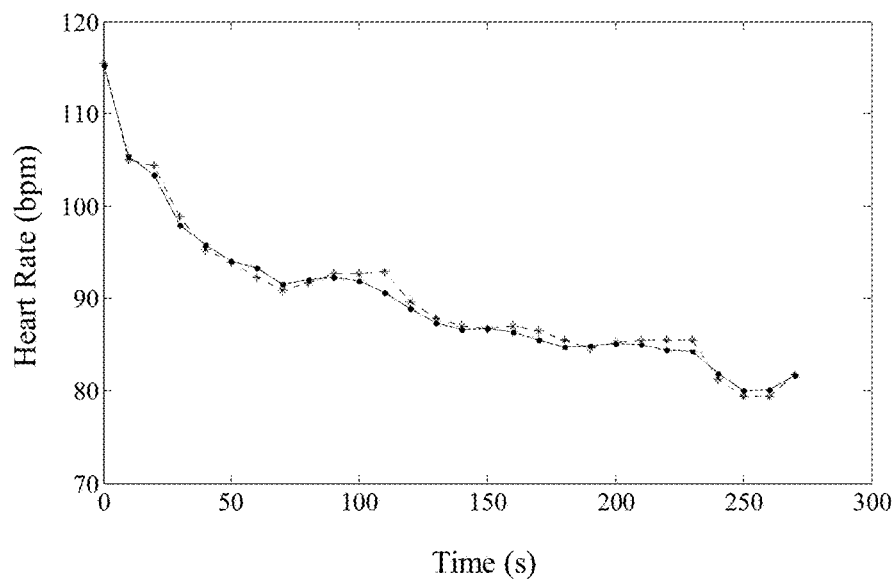
FIGS. 5A-5B illustrate the ability of the proposed methods to measure dynamic changes in both heart rate and respiration rate.
Figure 5B:
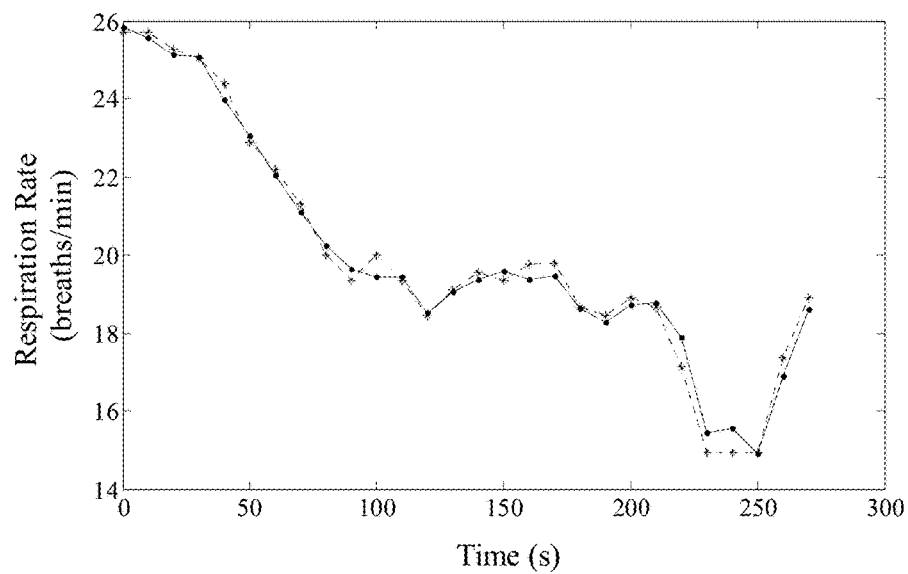

Following image capture, the images were analyzed, as described in Example 1, to obtain values for heart rate and respiration rate. These values were compared to the reference values for both heart rate and respiration rate obtained using the OnmiPlex® data acquisition system. The results are shown in FIGS. 5A-5B. Both heart rate and respiratory rate gradually decrease over time. The curves for both heart rate over time (FIG. 5A) and respiration rate over time (FIG. 5B) produced by image analysis closely matched values measured by the reference method throughout the test. The correlation coefficient was r=0.995 for both heart rate and respiratory rate. The RMSE for heart rate and respiratory rate were 0.15 and 0.06 respectively.

Example 3

Elimination of False Positives

To assess the ability of the method described above to distinguish between live human beings and inanimate human-shaped objects, both human subjects and inanimate human-shaped figures were imaged as described above. 1000 measurements were made from the captured images, with half of the measurements being obtained from imagery of live human subjects and half of the measurements being obtained from imagery of inanimate human-shaped figures.

Photographs of humans in magazines and drawings of a human face were used as fake figures.

The false positive rate was calculated as the total number of cases in which an inanimate human-shaped object was incorrectly identified as a human subject divided by the total number of inanimate human-shaped objects measured. The false negative rate was calculated as the total number of cases in which a human subject was incorrectly identified as an inanimate human-shaped object divided by the total number of human subjects measured.

During the experiment, the threshold for identification of a figure as an inanimate human-shaped figure was a difference of greater than 2 bpm between the values measured for heart rate by analysis of the two subsets of the ROI for heart rate. Overall, the false positive rate was found to be 0.6%, and the false negative rate was found to be 0.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A computer-implemented method for measuring one or more physiological parameters in a subject consisting of:

capturing a time series of digital single channel images of the subject with a night vision camera;

establishing a common region of interest in each of the digital images;

processing brightness of a common subset of pixels in each region of interest of each digital image and thereby producing a spatially averaged brightness of the common subset of pixels from each digital image;

combining the average brightness obtained from each digital image and thereby constructing a combined signal of average brightness over time showing changes in intensity over time;

processing the combined signal of average brightness over time using dynamical embedding and thereby constructing an embedding matrix from a series of delay vectors taken from the combined signal of average brightness over time;

processing the dynamical embedding matrix using independent component analysis and thereby identifying self-repeating rhythmicity from the combined signal of average brightness over time; and calculating the frequency of the self-repeating rhythmicity to identify the one or more physiological parameters of interest, wherein the one or more physiological parameters are selected from the group consisting of heart and respiration rates.

2. The method of claim 1, wherein the physiological parameters are measured simultaneously.

3. The method of claim 1, wherein the region of interest in each of the digital images is an area of the skin of the subject.

4. The method of claim 1, wherein the region of interest in each of the digital images is an area of the chest or abdomen of the subject.

5. The method of claim 1, further comprising detrending the single observed time series over time.

6. The method of claim 1, further comprising normalizing the single observed time series over time.

7. The method of claim 1, each vector comprises a subset of the single observed time series.

8. The method of claim 1, further comprising the step processing the regions of interest into two subsets;

performing the method of claim 1 on the two subsets to determine intrinsic oscillatory frequencies or each subset; and thereby determining the intrinsic oscillatory frequency of the first subset matches the intrinsic oscillatory frequency of the second subset, wherein in a mismatch indicates a false positive.

\* \* \* \* \*